United States Patent [19]

Henrick

[11] 4,323,574

[45] Apr. 6, 1982

[54] CIS AND TRANS ISOMERS OF α-METHYL(6-PHENOXY-2-PYRIDYL)-METHYL-3-(2,2-DICHLOROETHENYL)-2,2-DIMETHYLCYCLOPROPANECARBOXYLATES AND DERIVATIVES THEREOF

[75] Inventor: Clive A. Henrick, Palo Alto, Calif.

[73] Assignee: Zoecon Corporation, Palo Alto, Calif.

[21] Appl. No.: 209,912

[22] Filed: Nov. 24, 1980

[51] Int. Cl.$^3$ .................... A01N 43/40; C07D 213/64
[52] U.S. Cl. ...................................... 424/263; 546/302
[58] Field of Search ......................... 546/302; 424/263

[56] References Cited

U.S. PATENT DOCUMENTS 4,163,787  8/1979  Malhotra et al. .................... 424/263
4,221,799  9/1980  Van Heertum et al. ............ 424/263
4,238,614  12/1980  Henrick .............................. 546/301

*Primary Examiner*—Alan L. Rotman
*Attorney, Agent, or Firm*—Jacqueline S. Larson; Donald W. Erickson; Thomas T. Gordon

[57] ABSTRACT

The compounds α-methyl(6-phenoxy-2-pyridyl)methyl 3-(2,2-dichloroethenyl)-2,2-dimethylcyclopropanecarboxylate & S-α-methyl(6-phenoxy-2-pyridyl)methyl 3-(2,2-dichloroethenyl)-2,2-dimethylcyclopropanethiocarboxylate, synthesis thereof, & use of said compounds for the control of pests.

4 Claims, No Drawings

CIS AND TRANS ISOMERS OF α-METHYL(6-PHENOXY-2-PYRIDYL)METHYL-3-(2,2-DICHLOROETHENYL)-2,2-DIMETHYLCYCLOPROPANECARBOXYLATES AND DERIVATIVES THEREOF

This invention relates to novel pyridyl esters and S-thioesters of cyclopropanecarboxylic acid, synthesis thereof, and the use of said esters and thiolesters for the control of pests.

More particularly, the compounds of the present invention are represented by the following formula (A):

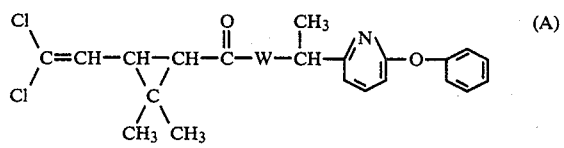

wherein, W is oxygen or sulfur.

The compounds of the present invention of formula (A) are useful agents for the control of pests such as insects and acarids. Additionally, the compounds of formula (A) have been found to possess greatly improved and extended residual activity upon exposure to the environment as compared with related prior art compounds, the most pertinent being those described by Malhotra and Ricks in U.S. Pat. No. 4,163,787.

The compounds of formula (A) where W is oxygen can be prepared by the reaction of an acid of formula I or the acid halide thereof with an alcohol of formula II. For example, the acid I is reacted with the alcohol II in the presence of a solvent such as methylene chloride, tetrahydrofuran, ether and the like, a catalyst such as 4-dimethylaminopyridine, and dicyclohexylcarbodiimide.

Alternatively, an acid of formula I is reacted with the halide, e.g., bromide, or mesylate corresponding to the alcohol II in the presence of a base such as potassium carbonate and the like in an organic solvent to prepare the esters of formula (A) (where W=oxygen).

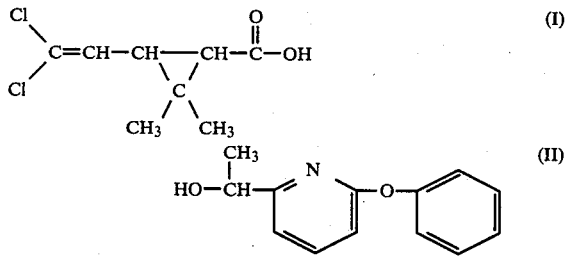

The acid of formula I is described by Hirano et al., U.S. Pat. No. 3,981,903, and by Punja, U.S. Pat. No. 3,979,519. The acid can be converted to the acid halide by conventional procedures. The alcohol of formula II is described by Henrick, U.S. Pat. No. 4,226,872.

The compounds of formula (A) where W is sulfur can be synthesized by reacting a thioacid of formula III with a halide, e.g. bromide or chloride, corresponding to the alcohol II. The reaction is conducted in an organic solvent such as hexamethylphosphoric triamide, dimethylformamide, N-methylpyrrolidone and the like in the presence of potassium carbonate, usually at an elevated temperature above room temperature, to form the S-thioester.

Alternatively, a carboxylic acid of formula I is reacted with a thiol of formula IV in the presence of, for example, 4-dimethylaminopyridine and dicyclohexylcarbodiimide.

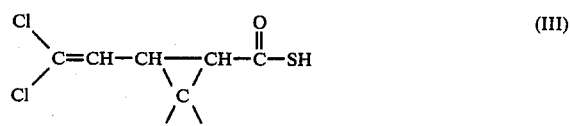

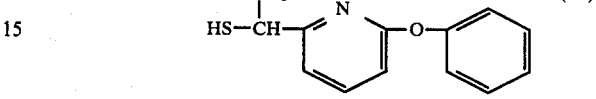

The S-thioacid III is prepared by reacting the corresponding carboxylic acid I with sodium hydrosulfide in an organic solvent such as dimethylformamide in the presence of triethylamine and ethyl chloroformate at a temperature below room tempeature.

The thiol IV can be prepared by first reacting a halide corresponding to the alcohol II with sodium hydrosulfide and hydrogen sulfide in the presence of a solvent such as ethanol. The intermediate product (V) is then reacted with a reducing agent such as zinc in acetic acid.

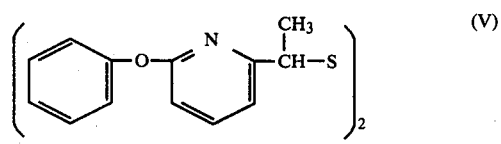

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of Formula A for combating insects and acarids for the protection of agricultural crops, for example soybeans, cotton, alfalfa, etc., a compound of formula A, or mixtures thereof, together with a carrier is applied to the pest or its habitat in a pesticidally effective amount. The carrier can be liquid or solid and include adjuvants such as wetting agents, dispersing agents and other surface active agents. The compounds of formula A can be used in formulations such a wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention of formula A demonstrate markedly improved control of pests over time under field conditions as compared to prior art compounds. This superior residual activity is important in that the compounds of formula A are more effective per application and fewer applications of the compounds are required over time for comparable control, resulting in savings in material and labor by the applicator.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

To a mixture of 0.3 g (1.40 mmol) of α-methyl-(6-phenoxy-2-pyridyl)methanol, 0.29 g (1.32 mmol) of 3-(2,2-dichloroethenyl)-2,2-dimethylcyclopropanecarboxylic acid, 0.013 g (0.104 mmol) of 4-dimethylaminopyridine and 3 ml of methylene chloride is added 0.27 g (1.3 mmol) of dicyclohexylcarbodiimide. This is stirred at RT for several hours, after which the solvent is removed by rotary evaporation. The residue is taken up in ether and filtered. The ether extract is washed with saturated sodium bicarbonate and with brine and is dried to yield α-methyl(6-phenoxy-2-pyridyl)methyl 3-(2,2-dichloroethenyl)-2,2-dimethylcyclopropanecarboxylate. Purification of the compound by thin layer chromatography (silica plate, developing with 20% ether/hexane) gives the isomers:

α-methyl(6-phenoxy-2-pyridyl)methyl cis-3-(2,2-dichloroethenyl)-2,2-dimethylcyclopropanecarboxylate and α-methyl-(6-phenoxy-2-pyridyl)methyl trans-3-(2,2-dichloroethenyl)-2,2-dicyclopropanecarboxylate.

EXAMPLE 2

3-(2,2-Dichloroethenyl)-2,2-dicyclopropanecarboxylic acid (1.0 g, 4.78 mmol) is dissolved in 25 ml of dry dimethylformamide and cooled, under nitrogen, to 0°–5°. Triethylamine (0.48 g, 4.78 mmol) is added in one portion, followed by addition of 0.52 g (4.78 mmol) of ethyl chloroformate. The slurry which forms is stirred for 20 minutes at 0°–5°, and then 1.07 g (9.6 mmol) of sodium hydrosulfide, partially dissolved in 10 ml of dimethylformamide, is added over 30 seconds. Stirring is continued for 2 hours at 0°–5° under nitrogen, after which the mixture is poured into 80 ml of water and 25 ml of ether is added. The aqueous layer is acidified to ~pH 2 with 5% sulfuric acid, followed by extraction with ether (3×). The combined ether extracts are washed with water (3×) and with brine, dried and stripped to give 3-(2,2-dichloroethenyl)-2,2-dimethylcyclopropanethiocarboxylic S-acid.

A mixture of 0.5 g (2.2 mmol) of 3-(2,2-dichloroethenyl)2,2-dicyclopropanethiocarboxylic S-acid, 0.62 g (2.2 mmol) of α-methyl(6-phenoxy-2-pyridyl)methyl bromide and 0.61 g (4.4 mmol) of potassium carbonate in 6 ml of dry hexamethylphosphoric triamide is heated, under nitrogen, at 40°–50° overnight. The mixture is then poured into cold water and extracted with ether (4×). The combined ether extracts are washed with water (3×) and with brine, dried and stripped. Purification by thin layer chromatography (silica gel, developing with 10% ethyl acetate/hexane) gives S-α-methyl(6-phenoxy-2-pyridyl)methyl 3-(2,2-dichloroethenyl)-2,2-dimethylcyclopropanethiocarboxylate.

EXAMPLE 3

A. Two groups of 10 each of 0–24 hr III instar *Heliothis virescens* larvae were treated with 1 μl of the test compound in acetone at different dosage rates by application to the dorsum of the thorax. Two groups of 10 each were treated identically with 1 μl acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control group using Abbott's formula. The toxicity is expressed as $LD_{50}$, which is the dosage, in μg per insect, required to kill 50% of the test insects. The compound α-methyl(6-phenoxy-2-pyridyl)methyl cis-3-(2,2-dichloroethenyl)-2,2-dimethylcyclopropanecarboxylate gave an $LD_{50}$ of less than 0.02 μg.

Following the same bioassay procedures, the compound S-α-methyl(6-phenoxy-2-pyridyl)methyl 3-(2,2-dichloroethenyl)2,2-dicyclopropanethiocarboxylate gave an $LD_{50}$ of less than 0.02 μg.

B. Fifteen 72-hr-old adult female *Musca domestica* L. are anesthetized with ether vapor. These are then treated with 1 μl of the test compound diluted to different dosage rates in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The toxicity, expressed as $LD_{50}$, of the compound α-methyl(6-phenoxy-2-pyridyl)methyl cis-3-(2,2-dichloroethenyl)-2,2-dimethylcyclopropanecarboxylate was less than 0.1 μg.

Following the same procedures, the compound S-α-methyl(6-phenoxy-2-pyridyl)methyl 3-(2,2-dichloroethenyl)-2,2-dimethylcyclopropanethiocarboxylate gave a $LD_{50}$ of less than 0.05 μg.

EXAMPLE 4

To determine the residual effect of the compounds of the present invention as compared to prior art compounds after exposure to ambient conditions out of doors for varying lengths of time, young four-leaf fava bean seedlings are sprayed to run-off with an aqueous 50 ppm (part-per-million) dilution (containing 0.025% Tween 20) of the test compound and held out of doors for 0, 7 or 14 days. After the exposure period, ten IIIrd instar *Heliothis virescens* larvae are caged on each plant and held for 3 days at 27° and 16 hours photoperiod. The effect is stated as the number dead calculated as a percentage of the total number exposed.

The residual effect over time of compounds of the present invention, α-methyl(6-phenoxy-2-pyridyl)methyl cis-3-(2,2-dichloroethenyl)-2,2-dimethylcyclopropanecarboxylate (Compound A) and α-methyl(6-phenoxy-2-pyridyl)methyl trans-3-(22-dichloroethenyl)-2,2-dimethylcyclopropanecarboxylate (Compound B), is compared with that of compounds disclosed by Malhotra & Ricks in U.S. Pat. No. 4,163,787, (6-phenoxyl-2-pyridyl)methyl cis-3-(2,2-dichloroethenyl)-2,2-dimethyl-cyclopropancarboxylate (Compound C) and (6-phenoxy-2-pyridyl)methyl trans-3-(2,2-dimethylcyclopropancarboxylate (Compound D). The results are shown in Table I.

TABLE 1
RESIDUAL EFFECTIVENESS OF SELECTED COMPOUNDS

| Compound | % Effect After | | |
|---|---|---|---|
| | 0 days | 7 days | 14 days |
| Control | 20 | 12 | 15 |
| A | 94 | 62 | 47 |
| B | 92 | 56 | 41 |
| C | 98 | 15 | 27 |
| D | 75 | 36 | 20 |

The above results illustrate the markedly superior control activity of the compounds of the present invention over those of the prior art after exposure out of doors.

What is claimed is:

1. A compound of the following formula (A):

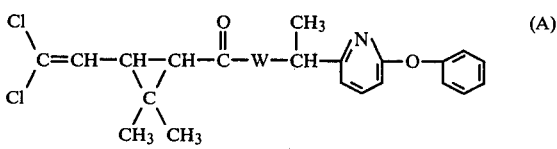

wherein, W is oxygen or sulfur.

2. The compound α-methyl(6-phenoxy-2-pyridyl)methyl 3-(2,2-dichloroethenyl)-2,2-dimethylcyclopropanecarboxylate, according to claim 1.

3. The compound S-α-methyl(6-phenoxy-2-pyridyl)methyl 3-(2,2-dichloroethenyl)-2,2-dimethylcyclopropanethiocarboxylate, according to claim 1.

4. A method for controlling insect or acarid pests which comprises applying to the pest or its habitat a pesticidally effective amount of a compound of claim 1.

* * * * *